United States Patent
Olivera et al.

(10) Patent No.: US 7,044,568 B2
(45) Date of Patent: May 16, 2006

(54) SURGICAL CONSOLE

(75) Inventors: Argelio M. Olivera, Los Alamitos, CA (US); Douglas T. Packard, Moorpark, CA (US)

(73) Assignee: Alcon, Inc., Hunenberg (CH)

( * ) Notice: Subject to any disclaimer, the term of this patent is extended or adjusted under 35 U.S.C. 154(b) by 583 days.

(21) Appl. No.: 10/236,601

(22) Filed: Sep. 5, 2002

(65) Prior Publication Data

US 2004/0046487 A1  Mar. 11, 2004

(51) Int. Cl.
*A47B 81/00* (2006.01)

(52) U.S. Cl. .............. 312/209; 312/249.12; 312/223.1; 312/249.8; 312/249.11

(58) Field of Classification Search ................ 312/209, 312/249.11, 249.12, 249.13, 249.8, 223.1, 312/7.2; 600/437; 297/217.3, 217.4, 217.5, 297/188.16, 188.15; 248/278.1, 286.1, 279.1, 248/314, 298.1
See application file for complete search history.

(56) References Cited

U.S. PATENT DOCUMENTS

| | | | |
|---|---|---|---|
| 4,437,677 A * | 3/1984 | Ksayian | 280/234 |
| 4,625,731 A | 12/1986 | Quedens et al. | |
| 5,028,746 A * | 7/1991 | Petrich | 191/12.2 R |
| 5,177,616 A * | 1/1993 | Riday | 348/837 |
| 5,179,447 A * | 1/1993 | Lain | 348/837 |
| 5,455,766 A | 10/1995 | Scheller et al. | |
| 5,627,584 A | 5/1997 | Nishikori et al. | |
| 5,667,179 A * | 9/1997 | Rosen | 248/278.1 |
| 5,924,988 A * | 7/1999 | Burris et al. | 600/437 |
| 6,007,036 A * | 12/1999 | Rosen | 248/286.1 |
| 6,022,088 A | 2/2000 | Metzler | |
| 6,024,427 A * | 2/2000 | Underwood et al. | 312/249.12 |
| 6,102,476 A * | 8/2000 | May et al. | 297/217.3 |
| 6,145,926 A * | 11/2000 | Lin | 297/217.3 |
| 6,179,263 B1* | 1/2001 | Rosen et al. | 248/278.1 |
| 6,220,658 B1* | 4/2001 | Lukawski et al. | 297/145 |
| 6,447,451 B1* | 9/2002 | Wing et al. | 600/437 |
| 6,510,049 B1* | 1/2003 | Rosen | 361/681 |
| 6,526,896 B1* | 3/2003 | Woronecki et al. | 108/95 |
| 6,587,333 B1* | 7/2003 | Tseng et al. | 361/681 |
| 2003/0023164 A1* | 1/2003 | Eichelberger et al. | 600/437 |

\* cited by examiner

*Primary Examiner*—Peter M. Cuomo
*Assistant Examiner*—Erika Garrett
(74) *Attorney, Agent, or Firm*—Jeffrey S. Schira

(57) ABSTRACT

A surgical console having a panel display mounted on a three-axis gimbel that permits articulation of the panel display via swivel, spin and tilt axes. The articulation mechanism uses two helix cable wraps with a single continuous cable that allows for large rotation of the panel display. The continuous cable simplifies construction and minimizes the electrical signal noise to the panel display.

13 Claims, 7 Drawing Sheets

SURGICAL CONSOLE

BACKGROUND OF THE INVENTION

This invention relates generally to the field of surgical consoles and, more particularly, to panel displays used on microsurgical consoles.

During modern surgery, particularly ophthalmic surgery, the surgeon uses a variety of pneumatic and electronically driven microsurgical handpieces. The handpieces are operated by a microprocessor-driven surgical console that receives inputs from the surgeon or an assistant by a variety of peripheral devices, such as footswitches, infrared remote control devices and touchscreen panel displays. With respect to touchscreen panel displays, these devices preferably are adjustable and prior art surgical consoles provide two axes of motion, swivel and tilt and, prior to the present invention, in order to provide these limited motions, the power supply and control signal cord needed to be separated into two or more independent, but connected pieces along its length. Such a construction adds undesirable complexity to the construction of the console, and unwanted electrical noise to the panel display.

Accordingly, a need continues to exist for a surgical console having a panel display that provides a simpler construction with reduced electrical noise.

BRIEF SUMMARY OF THE INVENTION

The present invention improves upon the prior art surgical consoles by providing a surgical console having a panel display mounted on a three-axis gimbel that permits articulation of the panel display via swivel, spin and tilt axes. The articulation mechanism uses two helix cable wraps with a single continuous cable that allows for large rotation of the panel display. The continuous cable simplifies construction and minimizes the electrical signal noise to the panel display.

Accordingly, one objective of the present invention is to provide a surgical console having a panel display mounted on a three-axis gimbel that permits articulation of the panel display via swivel, spin and tilt axes.

Another objective of the present invention is to provide a surgical console having a panel display mounted on an articulation mechanism uses two helix cable wraps that uses a single continuous cable that allows for large rotation of the panel display.

These and other advantages and objectives of the present invention will become apparent from the detailed description and claims that follow.

DETAILED DESCRIPTION OF THE INVENTION

Figure 1:
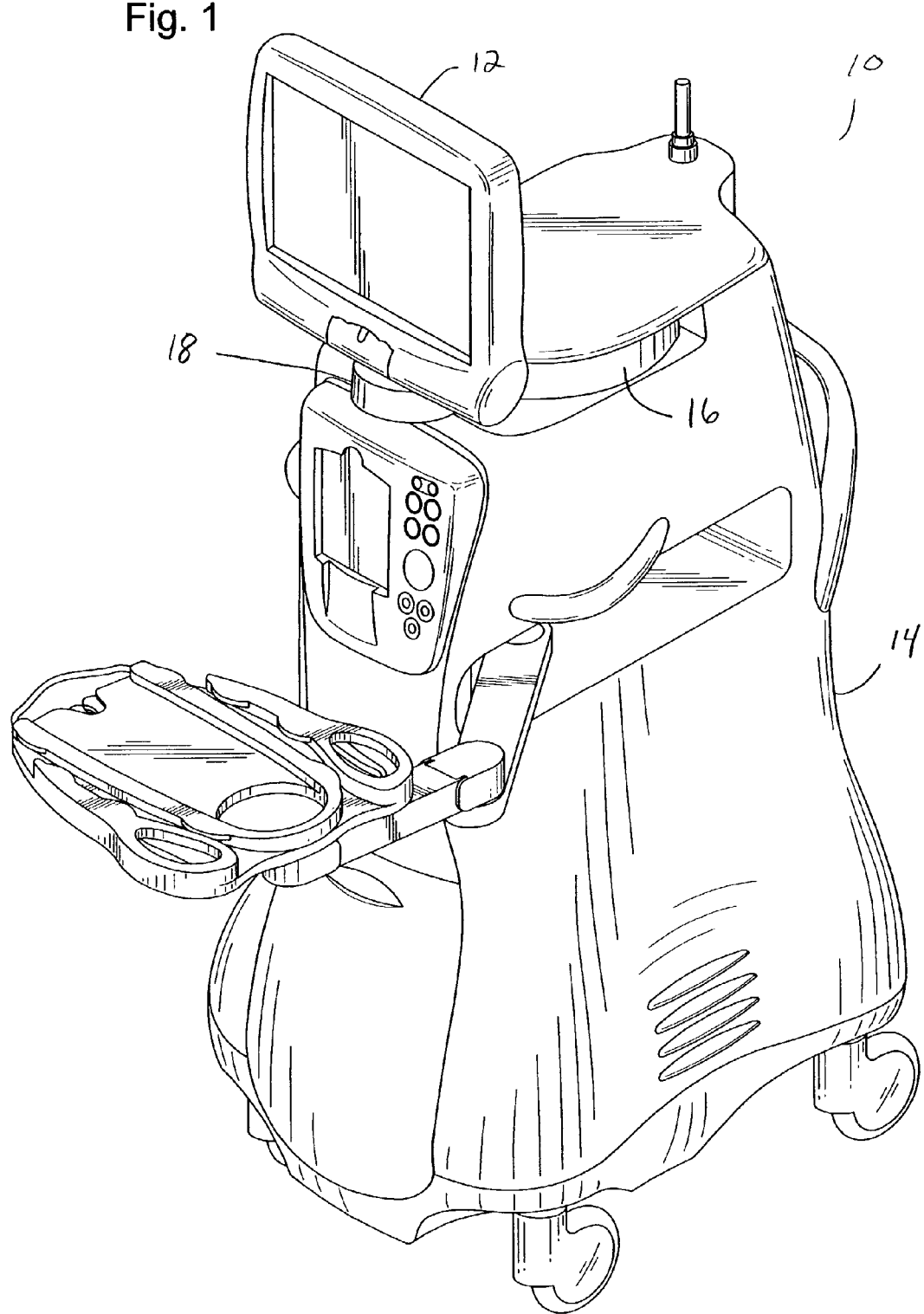
FIG. 1 is a perspective view of one embodiment of the surgical console of the present invention.
Figure 2:
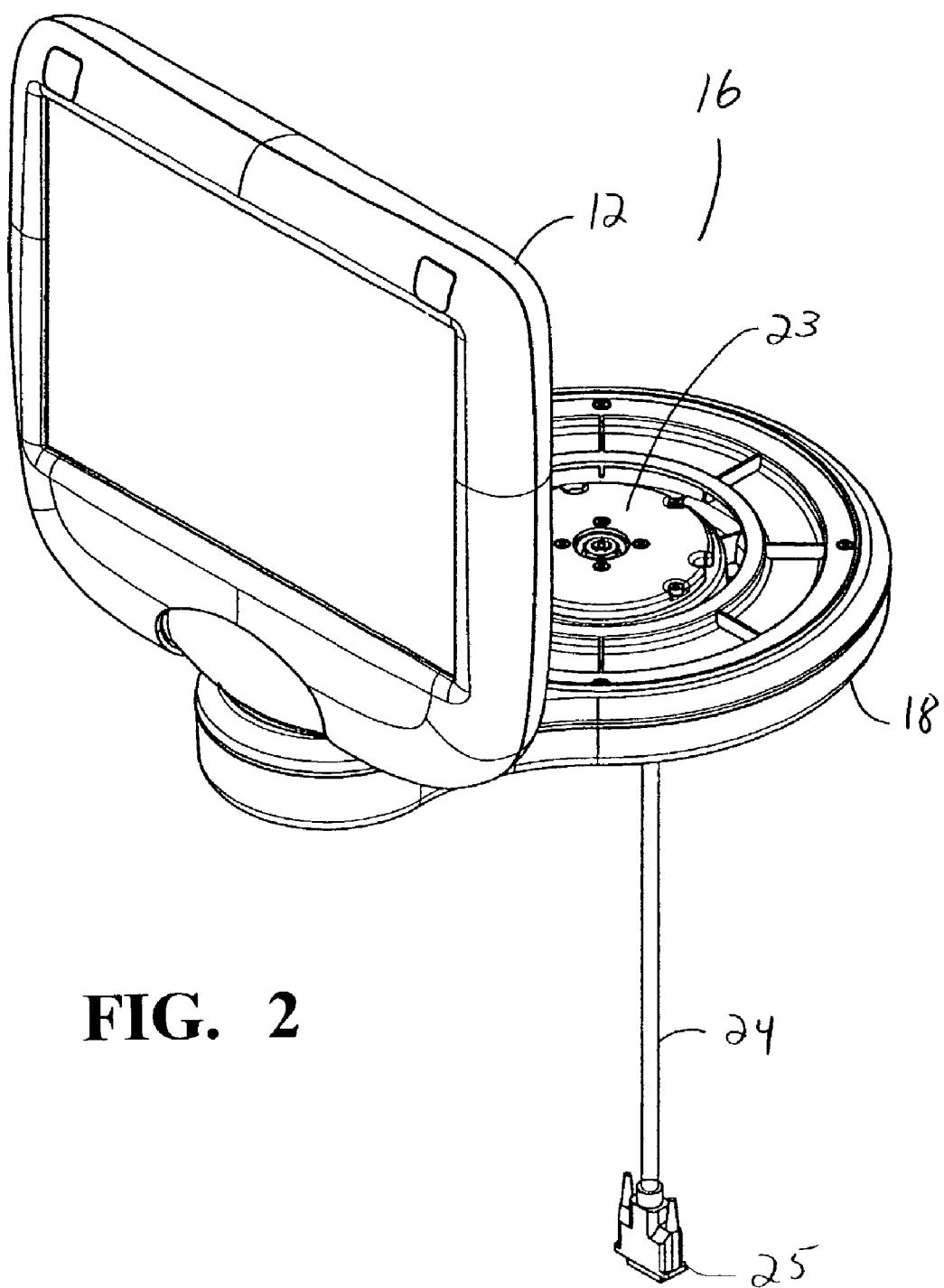
FIG. 2 is an assembled view of the panel display articulation mechanism of the present invention.

As best seen in FIG. 1, surgical console 10 of the present invention generally includes panel display 12 mounted to body 14 of console 10 by articulation mechanism 16. As best seen in FIGS. 2–7, articulation mechanism 16 generally includes base 18, upper spindle assembly 20 having upper cable wrap 21, lower spindle assembly 23 having lower cable wrap 22 and cable 24. Upper spindle assembly 20 may be of any suitable design, but generally includes shaft 19 along with a suitable drag brake (not shown). Cable 24 preferably is of one continuous, uninterrupted length and has connectors 25 on either end for connecting display 12 to console 10 through articulation mechanism 16.

Figure 3:
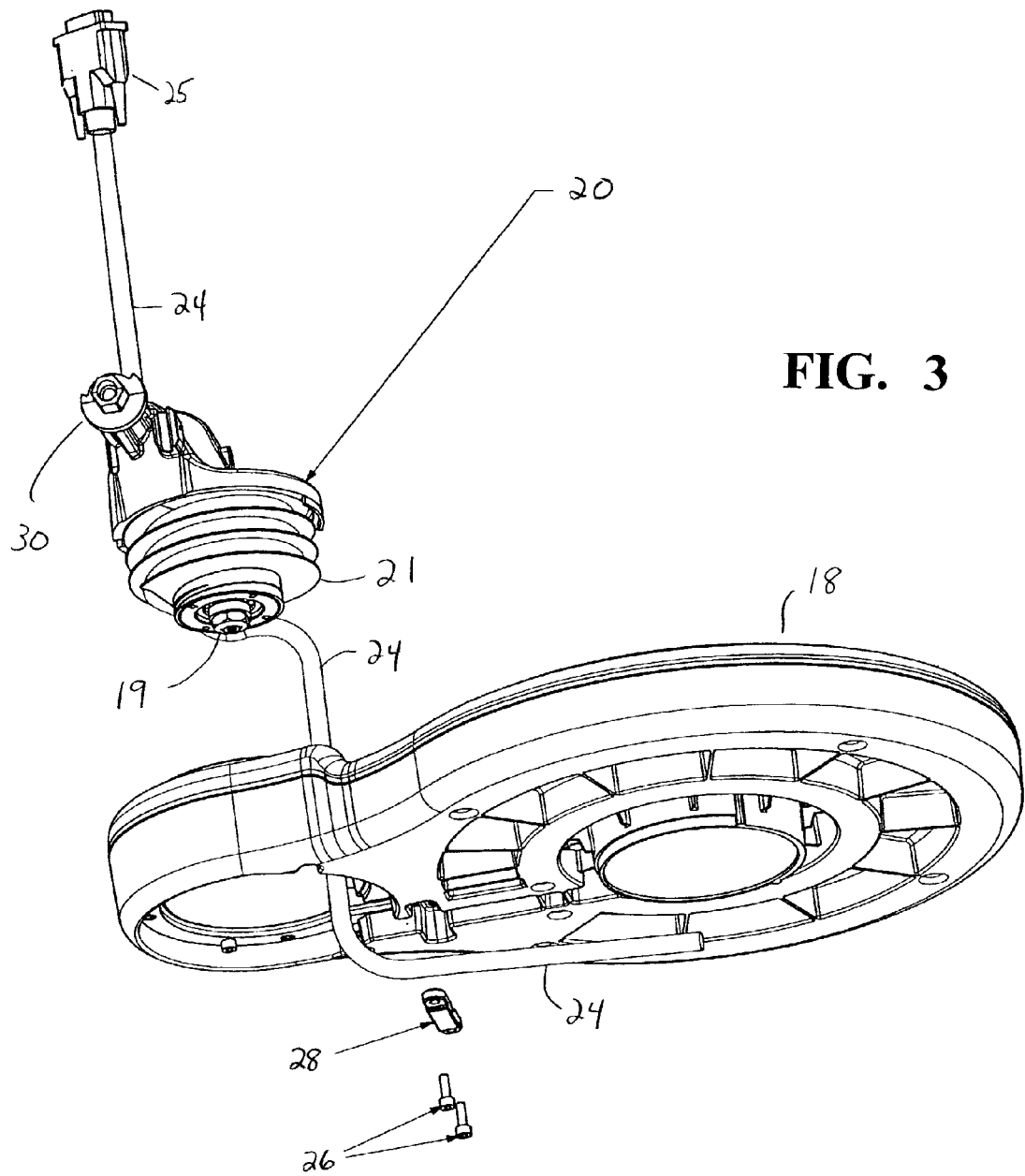
FIG. 3 is an exploded, partial assembly view of the panel display articulation mechanism of the present invention illustrating a first cable wrap mechanism.
Figure 4:
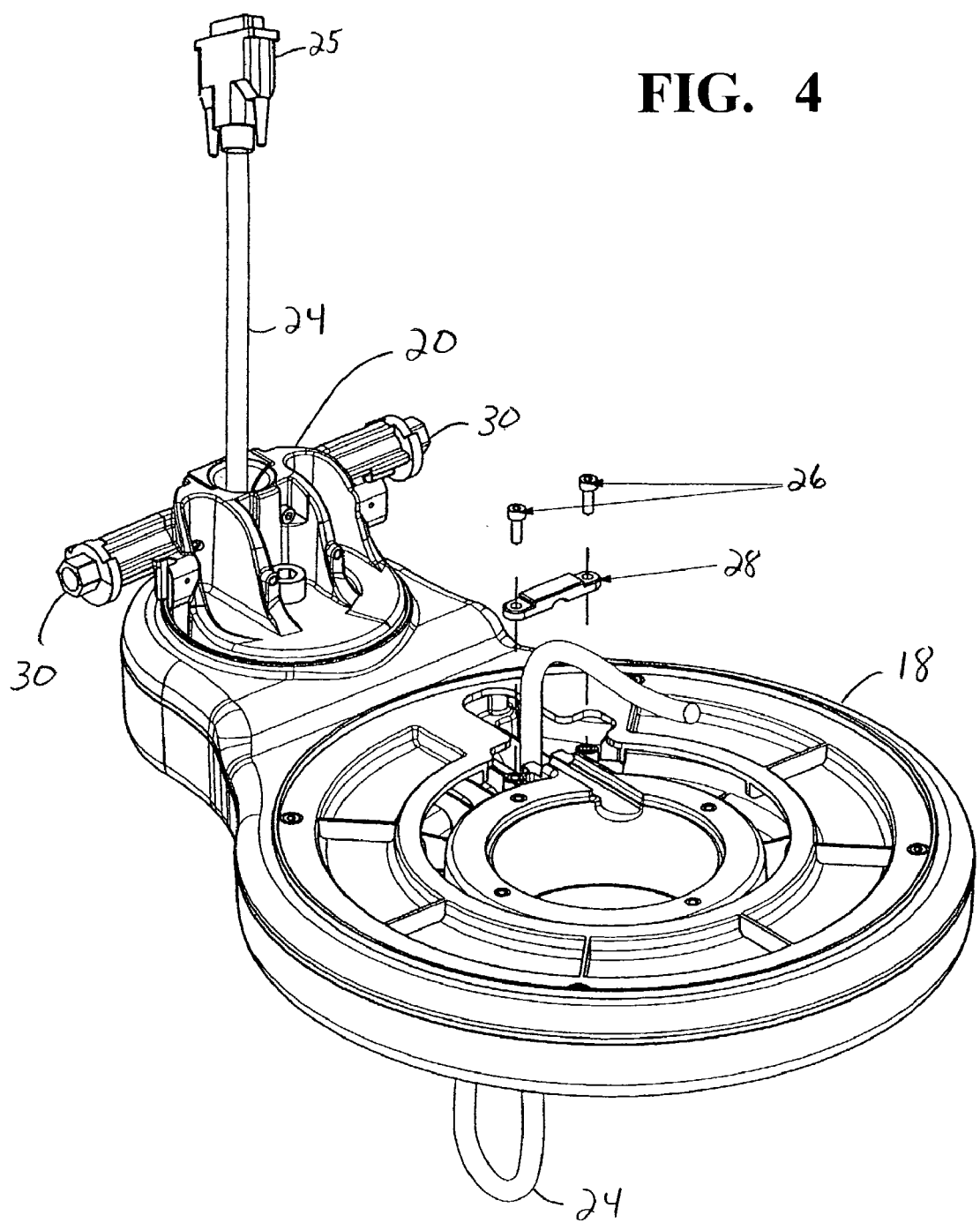
FIG. 4 is an exploded, partially assembled view of the panel display articulation mechanism of the present invention illustrating the cable routing.
Figure 7:
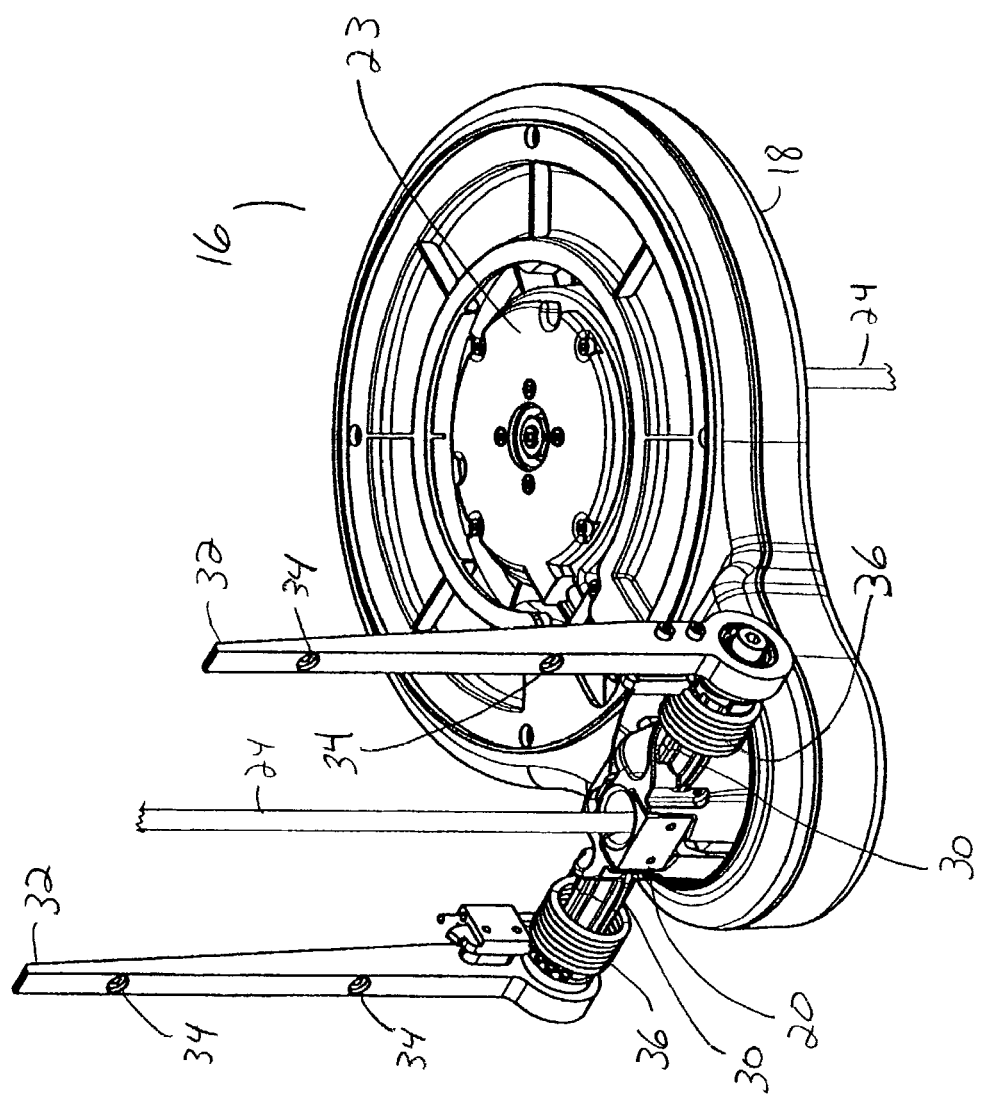
FIG. 7 is a perspective view of the assembled articulation mechanism of the present invention.

As best seen in FIGS. 3 and 4, cable 24 wraps around helix upper cable wrap 21 in upper spindle assembly 20 and is held in place by screws 26 and clamps 28 in base 18. Upper cable wrap 21 allows panel 12 spin on upper spindle assembly 20 without straining or damaging cable 24. Upper spindle assembly 20 allows panel display 12 to spin about spindle 19 through at least 90° of motion and preferably at least 225° of motion. Upper spindle assembly 20 also contains pivot arms 30. As best seen in FIG. 7, vertical mounting arms 32 are rotationally mounted on pivot arms 30 and contain mounting holes 34 for allowing the mounting of panel display 12 on mounting arms 32. Mounting arms 32 allow for tilting on panel display 12, such action being assisted by springs 36 slidably received on pivot arms 30. Springs 36 also have a gravity compensating function, preventing the weight of panel display 12 from rotating panel display 12 downward. In addition, pivot arms 30 may contain a suitable drag brake (not shown). Preferably, pivot arms 30 and mounting arms 32 allow enough range of motion so as to allow panel display 12 to tilt forward and tilt backward to fold flat against base 18, preferably at least 95° of motion.

Figure 5:
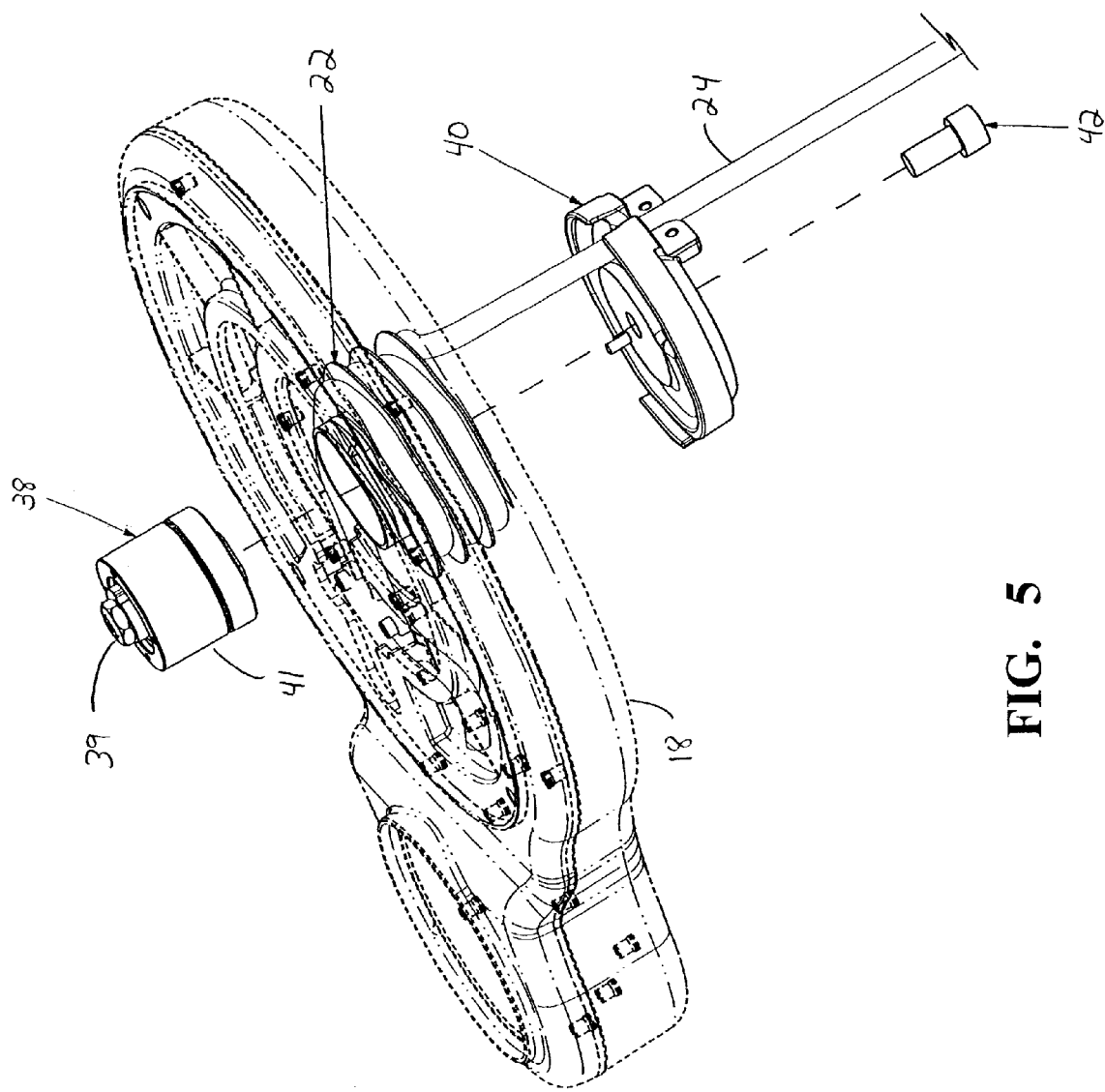
FIG. 5 is an exploded, partial assembly view of the panel display articulation mechanism of the present invention illustrating a second cable wrap mechanism.
Figure 6:
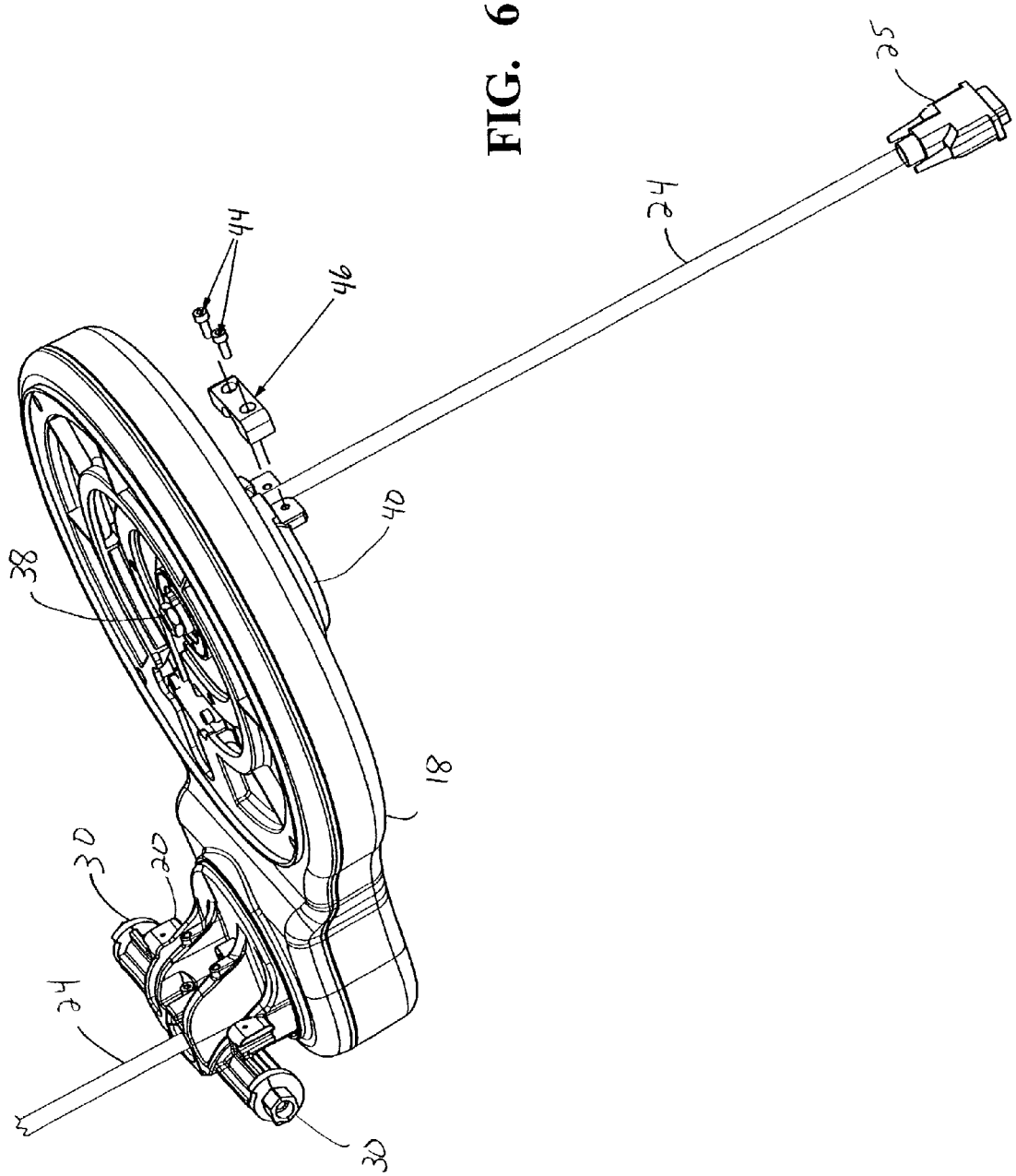
FIG. 6 is an exploded, partially assembled view of the panel display articulation mechanism of the present invention illustrating the cable routing.

As best seen in FIGS. 5 and 6, lower spindle assembly 23 contains spindle 38, clamping plate 40, screw 42 and lower cable wrap 22. Spindle 38 may be of any suitable design, but generally includes shaft 39, housing 41 and a suitable drag brake (not shown). Screw 42 is received through clamping plate 40, lower cable wrap 22, base 18 and into spindle 38. Cable 24 is fix to clamping plate 40 by screws 44 and clamp 46. Spindle 38 and lower cable wrap 22 operate within base 18 in the manner described above to allow rotation (swivel) of lower base 18 on console 10, preferably, through at least 90° of motion and more preferable, through at least 180° of motion.

In use, assembly 16 of the present invention allow panel display 12 to rotate along three axes, spin (about upper spindle assembly 20), tilt (about pivot arms 30) and swivel (about lower spindle assembly 23). Upper cable wrap 21 and lower cable wrap 22 coil cable 24 in a helix shape, allowing for rotation of upper spindle assembly 20 and lower spindle assembly 23 without straining or damaging cable 24. Such a construction also allows the use of a continuous, uninterrupted cable 24, with no intermediate breaks or connections between console 10 and panel display 12, thereby simplifying construction and reducing unwanted electrical noise to panel display 12.

This description is given for purposes of illustration and explanation. It will be apparent to those skilled in the relevant art that modifications may be made to the invention as herein described without departing from its scope or spirit.

We claim:

1. A surgical console, comprising:
   a) a body having an exterior;
   b) a panel display mounted to the exterior of the body by an articulation mechanism, the articulation mechanism allowing for movement of the panel display along at least three axes wherein the articulation mechanism includes at least one spindle assembly; and
   c) a helical cable wrap contained in the spindle assembly.

2. The console of claim 1 wherein the cable wrap permits a cable connecting the panel display to the body to be of one continuous, uninterrupted length.

3. The console of claim 1 wherein the three axes of motion are tilt, spin and swivel and the articulation mechanism allows for spin and swivel of the panel display through at least 90° of motion.

4. The console of claim 3 wherein the articulation mechanism allows for swivel of the panel display through at least 180° of motion.

5. The console of claim 3 wherein the articulation mechanism allows for spin of the panel display through at least 225° of motion.

6. The console of claim 3 wherein the articulation mechanism allows for at least 95° of tilt of the panel display.

7. A surgical console, comprising:
   a) a body having an exterior;
   b) a panel display mounted to the exterior of the body by an articulation mechanism, the articulation mechanism containing upper and lower spindle assemblies and allowing for tilt, spin and swivel of the panel display along at least three axes; and
   c) upper and lower helical cable wraps, contained in the upper and lower spindle assemblies, respectively.

8. The console of claim 7 wherein the upper spindle assembly mounts the panel display to the articulation mechanism and the lower spindle assembly mounts the articulation mechanism to the body of the console.

9. The console of claim 7 wherein the cable wraps permitting a cable connecting the panel display to the body to be of one continuous, uninterrupted length.

10. The console of claim 7 wherein the articulation mechanism allows for spin and swivel of the panel display through at least 90° of motion.

11. The console of claim 7 wherein the articulation mechanism allows for at least 95° of tilt of the panel display.

12. The console of claim 10 wherein the articulation mechanism allows for swivel of the panel display through at least 180° of motion.

13. The console of claim 10 wherein the articulation mechanism allows for spin of the panel display through at least 225° of motion.

* * * * *